United States Patent

Neves

Patent Number: 6,102,051
Date of Patent: Aug. 15, 2000

[54] FLOSSING KIT

[76] Inventor: Paul S. Neves, 71 Home St., Malden, Mass. 02148

[21] Appl. No.: 09/339,781

[22] Filed: Jun. 24, 1999

[51] Int. Cl.[7] .................................................. A61C 15/00
[52] U.S. Cl. .......................... 132/321; 132/323; 206/63.5
[58] Field of Search ..................................... 132/323, 324, 132/329, 321; 206/368, 369, 63.5

[56] References Cited

U.S. PATENT DOCUMENTS

| D. 284,896 | 7/1986 | Ching-chou | 132/323 |
|---|---|---|---|
| 407,362 | 7/1889 | Mason | 132/321 |
| 577,468 | 2/1897 | Tissington | 132/323 |
| 2,083,398 | 6/1937 | Rohland | 132/321 |
| 3,438,486 | 4/1969 | Pinkas | 206/369 |
| 4,105,120 | 8/1978 | Bradberry | 132/323 |
| 4,579,221 | 4/1986 | Corella | 206/63.5 |
| 5,184,631 | 2/1993 | Ikeda | 132/323 |
| 5,322,077 | 6/1994 | Corella | 132/323 |
| 5,433,227 | 7/1995 | Chen | 132/323 |
| 5,549,201 | 8/1996 | Braude | 206/63.5 |
| 5,738,125 | 4/1998 | Lin | 132/323 |

*Primary Examiner*—Todd E. Manahan

[57] ABSTRACT

A flossing kit for providing disposable devices for flossing a user's teeth. The flossing kit includes a first flossing device comprising an elongate shaft having a pair of opposite ends and a generally V-shaped floss holder coupled to a first of the ends of the shaft. The floss holder has a pair of elongate arms each having a terminal end. An elongate filament is extended between the terminal ends of the arms of the floss holder. The shaft of the first flossing device also tapers to a toothpick point adjacent a second of the ends of the shaft.

1 Claim, 3 Drawing Sheets

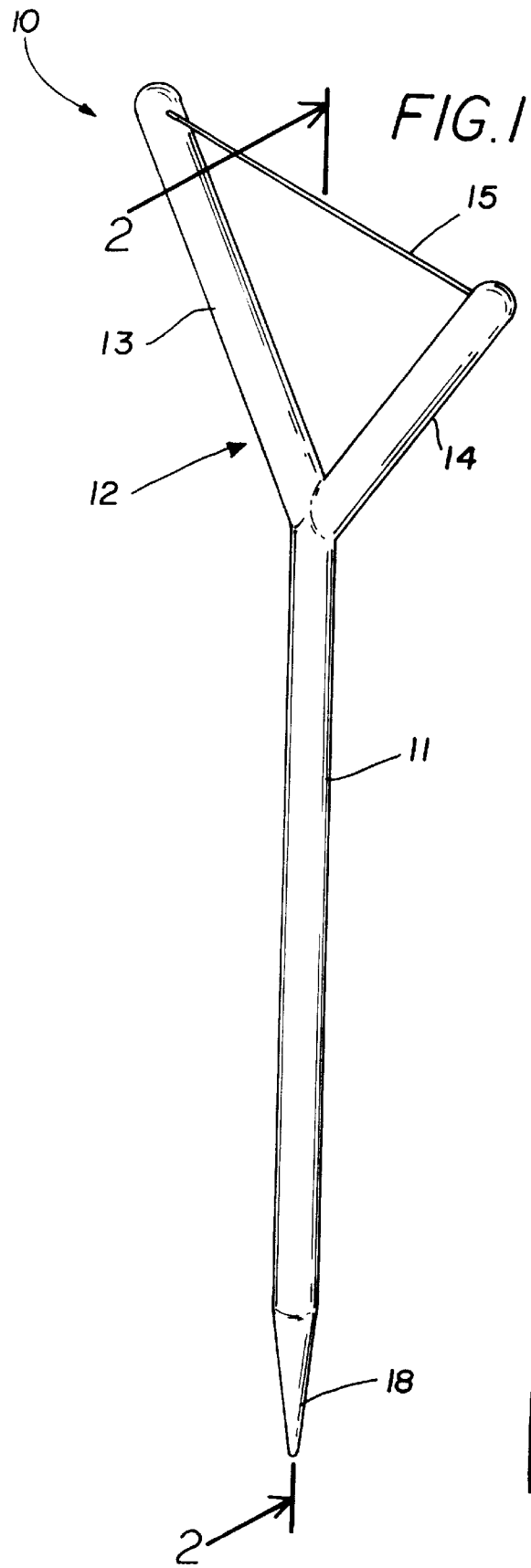
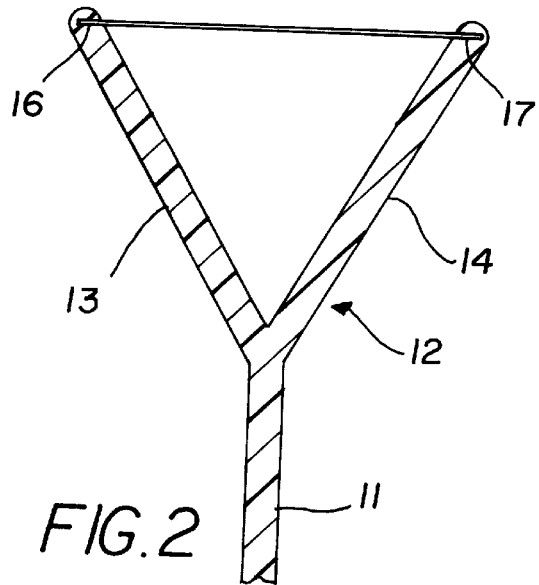
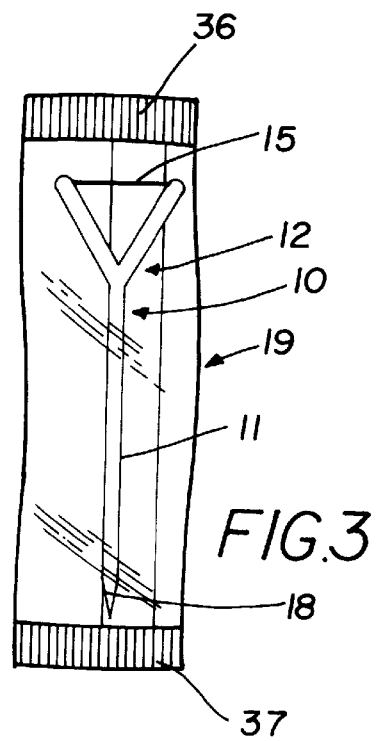

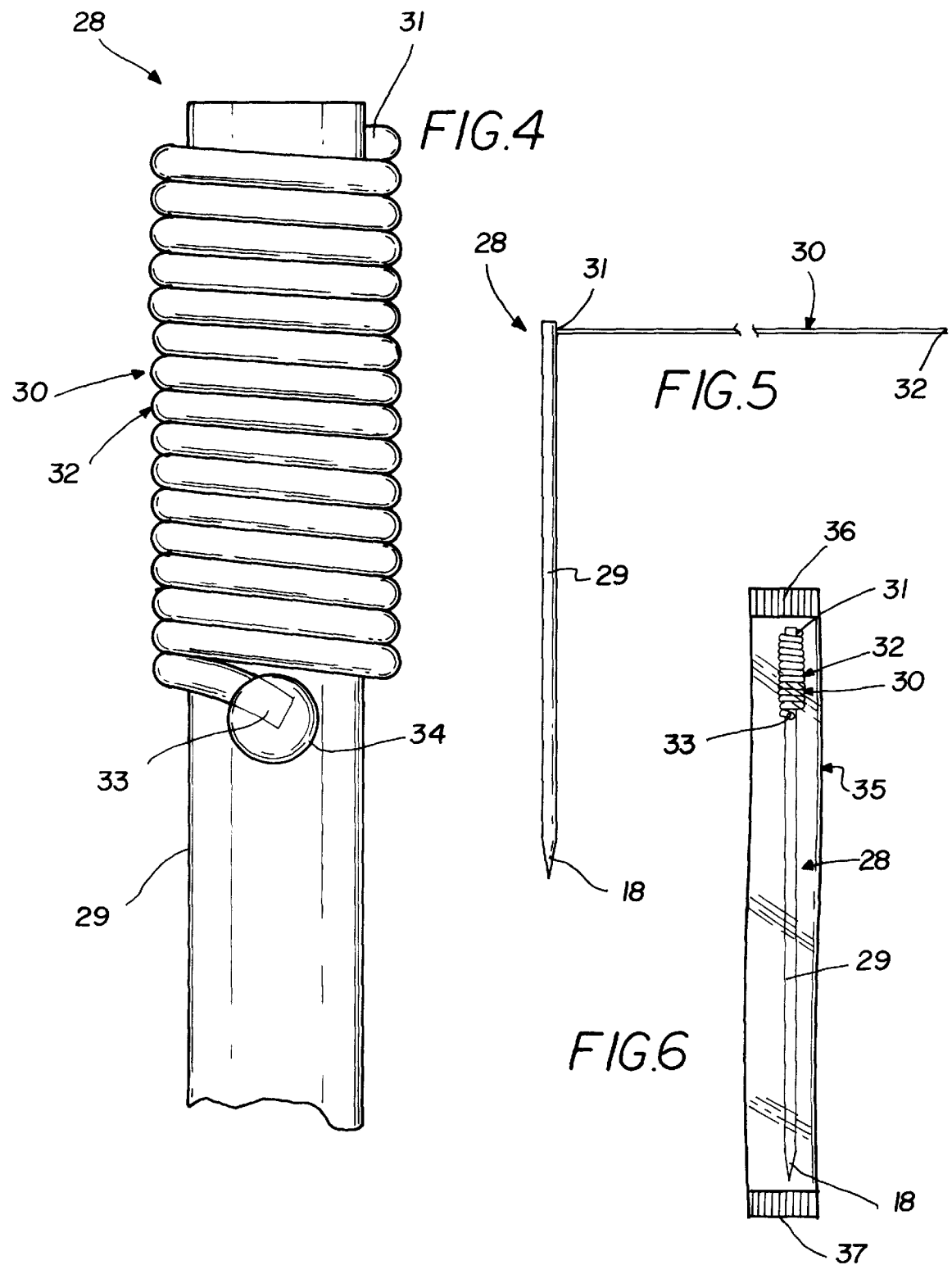

FLOSSING KIT

BACKGROUND OF THE INVENTION

1. Field of the Invention

The present invention relates to dental flossing devices and more particularly pertains to a new flossing kit for providing disposable devices for flossing a user's teeth.

2. Description of the Prior Art

The use of dental flossing devices is known in the prior art. More specifically, dental flossing devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,162,687; U.S. Pat. No. 250,430; U.S. Pat. No. 1,506,010; U.S. Pat. No. 5,738,125; U.S. Pat. No. 2,443,415; and U.S. Pat. No. Des. 312,710.

While these devices fulfill their respective, particular objectives and requirements, the aforementioned patents do not disclose a new flossing kit. The inventive device includes a first flossing device comprising an elongate shaft having a pair of opposite ends and a generally V-shaped floss holder coupled to a first of the ends of the shaft. The floss holder has a pair of elongate arms each having a terminal end. An elongate filament is extended between the terminal ends of the arms of the floss holder. The shaft of the first flossing device also tapers to a toothpick point adjacent a second of the ends of the shaft.

In these respects, the flossing kit according to the present invention substantially departs from the conventional concepts and designs of the prior art, and in so doing provides an apparatus primarily developed for the purpose of providing disposable devices for flossing a user's teeth.

SUMMARY OF THE INVENTION

In view of the foregoing disadvantages inherent in the known types of dental flossing devices now present in the prior art, the present invention provides a new flossing kit construction wherein the same can be utilized for providing disposable devices for flossing a user's teeth.

The general purpose of the present invention, which will be described subsequently in greater detail, is to provide a new flossing kit apparatus and method which has many of the advantages of the dental flossing devices mentioned heretofore and many novel features that result in a new flossing kit which is not anticipated, rendered obvious, suggested, or even implied by any of the prior art dental flossing devices, either alone or in any combination thereof.

To attain this, the present invention generally comprises a first flossing device comprising an elongate shaft having a pair of opposite ends and a generally V-shaped floss holder coupled to a first of the ends of the shaft. The floss holder has a pair of elongate arms each having a terminal end. An elongate filament is extended between the terminal ends of the arms of the floss holder. The shaft of the first flossing device also tapers to a toothpick point adjacent a second of the ends of the shaft.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new flossing kit apparatus and method which has many of the advantages of the dental flossing devices mentioned heretofore and many novel features that result in a new flossing kit which is not anticipated, rendered obvious, suggested, or even implied by any of the prior art dental flossing devices, either alone or in any combination thereof.

It is another object of the present invention to provide a new flossing kit which may be easily and efficiently manufactured and marketed.

It is a further object of the present invention to provide a new flossing kit which is of a durable and reliable construction.

An even further object of the present invention is to provide a new flossing kit which is susceptible of a low cost of manufacture with regard to both materials and labor, and which accordingly is then susceptible of low prices of sale to the consuming public, thereby making such flossing kit economically available to the buying public.

Still yet another object of the present invention is to provide a new flossing kit which provides in the apparatuses and methods of the prior art some of the advantages thereof, while simultaneously overcoming some of the disadvantages normally associated therewith.

Still another object of the present invention is to provide a new flossing kit for providing disposable devices for flossing a user's teeth.

Yet another object of the present invention is to provide a new flossing kit which includes a first flossing device comprising an elongate shaft having a pair of opposite ends and a generally V-shaped floss holder coupled to a first of the ends of the shaft. The floss holder has a pair of elongate arms each having a terminal end. An elongate filament is extended between the terminal ends of the arms of the floss holder. The shaft of the first flossing device also tapers to a toothpick point adjacent a second of the ends of the shaft.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic perspective view of a first flossing device of a flossing kit according to the present invention.

FIG. 2 is a schematic cross sectional view of the first flossing device taken from the vantage of line 2—2 of FIG. 1.

FIG. 3 is a schematic side view of the first flossing device enclosed in a tearable packet.

FIG. 4 is a schematic enlarged side view of an end of a third flossing device of the present invention with the elongate filament in a coiled form about the shaft.

FIG. 5 is a schematic side view of the third flossing device with the elongate filament uncoiled and extended for ready use in flossing a user's teeth.

FIG. 6 is a schematic side view of the third flossing device, enclosed in a tearable packet.

DETAILED DESCRIPTION OF THE INVENTION

Figure 7:
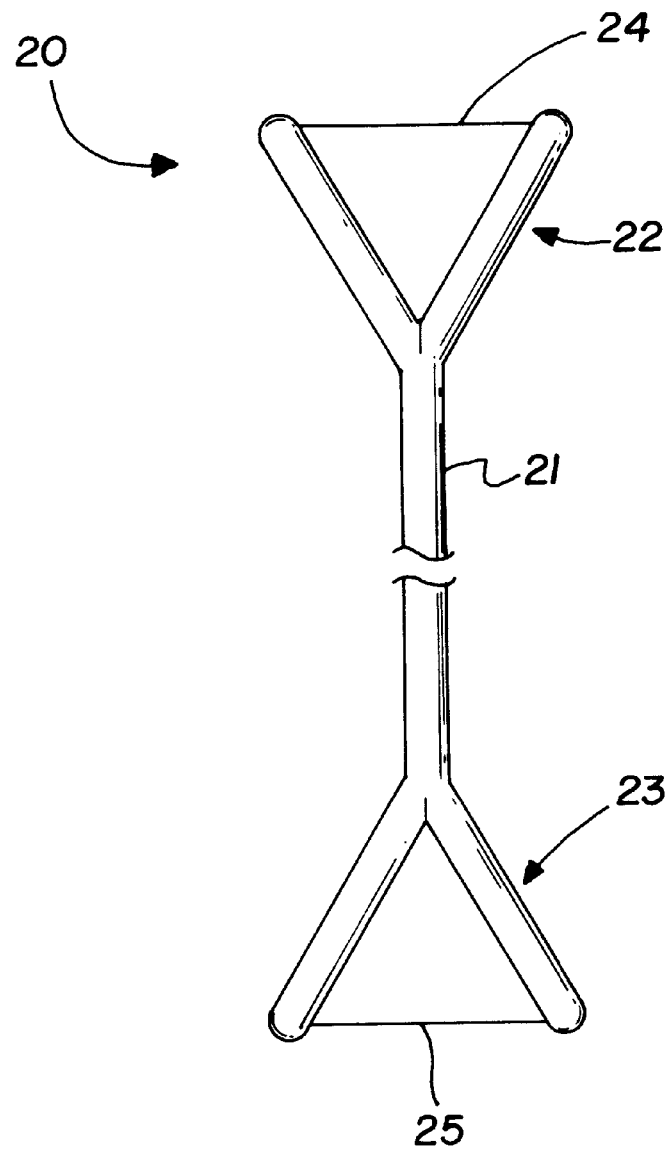
FIG. 7 is a schematic side view of a second flossing device of the present invention.

With reference now to the drawings, and in particular to FIGS. 1 through 8 thereof, a new flossing kit embodying the principles and concepts of the present invention will be described.

As best illustrated in FIGS. 1 through 8, the flossing kit generally includes a first flossing device comprising an elongate shaft having a pair of opposite ends and a generally V-shaped floss holder coupled to a first of the ends of the shaft. The floss holder has a pair of elongate arms each having a terminal end. An elongate filament is extended between the terminal ends of the arms of the floss holder. The shaft of the first flossing device also tapers to a toothpick point adjacent a second of the ends of the shaft.

With reference to FIGS. 1, 2, and 3, the flossing kit includes a first flossing device 10 which has an elongate shaft 11 with a pair of opposite ends.

A generally V-shaped floss holder 12 is coupled to a first of the ends of the shaft. The floss holder has a pair of elongate arms 13,14. In one embodiment of the first flossing device, the arms of the floss holder may be extended at an acute angle to each other.

Each of the arms of the floss holder has a terminal end. An elongate filament 15 is extended between the terminal ends of the arms of the floss holder. The elongate filament may comprise a length of dental floss. The elongate filament has a pair of opposite ends 16,17. As best illustrated in FIG. 2, one of the ends of the elongate filament is embedded in the terminal end of one of the arms of the floss holder and the other of the ends of the elongate filament is embedded in the terminal end of the other of the arms of the floss holder to couple the ends of the elongate filament to the terminal ends of the arms of the floss holder.

The shaft of the first flossing device tapers to a toothpick point 18 adjacent a second of the ends of the shaft, the point is designed for serving as a toothpick.

In one illustrative embodiment, the first flossing device may have a length defined between a plane in which the terminal ends of the arms of the floss holder lie and the second end of the shaft of about 2 inches.

As illustrated in FIG. 3, a first packet 19 may enclose the first flossing device therein. The first packet may comprise a tearable material such as a cellophane sheet material and also may comprise a translucent material to permit viewing therethrough of the first flossing device.

With particular reference to FIG. 7, the kit may also include a second flossing device 20 comprising an elongate shaft 21 with a pair of opposite ends. Each of the ends of the shaft of the second flossing device has a generally V-shaped floss holder 22,23 coupled thereto of similar construction and configuration as the floss holder of the first flossing device. Thus, each of the floss holders has a pair of elongate arms that may be extended at an acute angle to each other. Each of the arms of each floss holder has a terminal end.

In the second flossing device, each of the floss holders has an elongate filament 24,25 each comprising a length of dental floss that is extended between the terminal ends of the arms of the respective floss holder just as in the case of the floss holder of the first flossing device. Like in the case of the first flossing device, one end of each elongate filament of the second flossing device is embedded in the terminal end of one of the arms of the respective floss holder and the other end of each elongate filament is embedded in the terminal end of the other of the arms of respective floss holder to couple the ends of the elongate filaments to the terminal ends of the arms of the respective floss holders.

Like the first flossing device, the second flossing device may also have a length of about 2 inches. Additionally, a packet just like the first packet may enclose the second flossing device therein.

Figure 8:
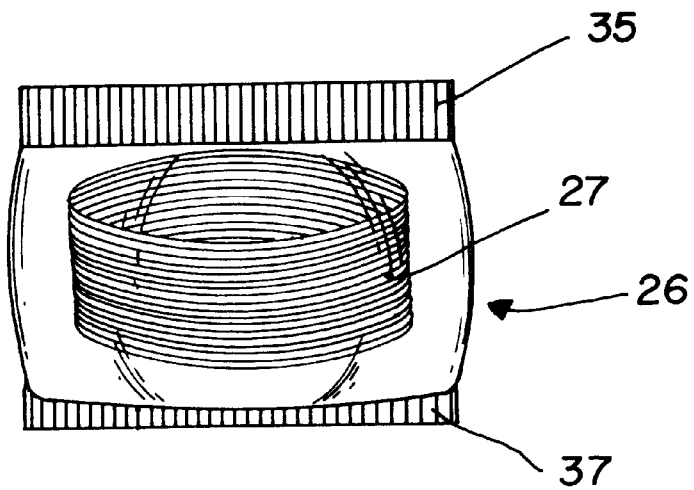
FIG. 8 is a schematic side view of a packet enclosing an elongate filament of the flossing kit.

Turning to FIG. 8, the flossing kit may also include a second packet 26 enclosing therein an elongate filament 27 wound into a coil. The elongate filament in the second packet comprises a length of dental floss. In one embodiment, the length of dental floss in the second packet may be about 12 inches long. In use, the second packet may be torn open to permit removal of the elongate filament so that a user may use it to floss their teeth therewith.

The flossing kit may also include a third flossing device 28 as illustrated in FIGS. 4, 5, and 6. The third flossing device comprises an elongate shaft 29 having a pair of opposite ends. The third flossing device may have a length defined between the ends of the shaft of about 2 inches.

The third flossing device also includes an elongate filament 30 comprising a length of dental floss. In one embodiment, the length of dental floss may be about 12 inches long which is appropriate for a single flossing of the user's teeth.

The elongate filament of the third flossing device has a pair of opposite ends. A first end 31 of the pair of ends of the elongate filament is embedded in a first of the ends of the shaft to couple the first end of the elongate filament to the shaft. As illustrated in FIG. 4, the elongate filament is wound about the shaft adjacent the first end of the shaft to form a coil 32 around the shaft.

A second end 33 of the pair of ends of the elongate filament is detachably attached to the shaft when the elongate filament is in the coiled configuration. In one embodiment, a bead of wax 34 may be applied to the second end of the elongate filament and the shaft to detachably attach the second end of the elongate filament to the shaft. In use, the second end of the elongate filament is detachable from the shaft upon peeling or picking of the bead of wax off of the shaft to free the second end of the elongate filament. As illustrated in FIG. 5, the elongate filament may then be unwound from the shaft after the bead of wax is removed to provide an elongate portion of the elongate filament which may be used to floss a user's teeth therewith.

The shaft of the third flossing device tapers to a toothpick point 35 adjacent a second of the ends of the shaft. Like the toothpick point of the first flossing device, the toothpick point of the third flossing device is designed for serving as a toothpick.

With reference to FIG. 6, a third packet 35 may be provided to enclose the third flossing device therein. The third packet is similar to the other packets of the kit and comprises a tearable material such as a cellophane sheet material and a translucent material to permit viewing therethrough of the third flossing device.

Each of the packets may have a pair of heat sealed ends 36,37 to close the respective packet after insertion of the associated flossing device therein. The packets allow a user to carry individual flossing devices of the kit in a sanitary fashion until the particular device is needed for flossing the user's teeth.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A flossing kit, comprising:

a first flossing device, comprising:

an elongate shaft having a pair of opposite ends;

a generally V-shaped floss holder coupled to a first of said ends of said shaft, said floss holder having a pair of elongate arms;

said arms of said floss holder being extended at an acute angle to each other;

each of said arms of said floss holder having a terminal end;

an elongate filament being extended between said terminal ends of said arms of said floss holder, said elongate filament comprising a length of dental floss;

said elongate filament having a pair of opposite ends;

one of said ends of said elongate filament being embedded in said terminal end of one of said arms of said floss holder and the other of said ends of said elongate filament being embedded in said terminal end of the other of said arms of said floss holder;

said shaft tapering to a toothpick point adjacent a second of said ends of said shaft;

said first flossing device having a length defined between a plane in which said terminal ends of said arms of said floss holder lie and said second end of said shaft of about 2 inches; and a first packet enclosing said first flossing device therein, said first packet comprising a tearable material, said first packet comprising a translucent material to permit viewing therethrough of said first flossing device;

a second flossing device, comprising:

an elongate shaft having a pair of opposite ends;

each of said ends of said shaft having a generally V-shaped floss holder coupled thereto;

each of said floss holder having a pair of elongate arms;

said arms of said floss holder being extended at an acute angle to each other;

each of said arms of said floss holder having a terminal end;

each of said floss holders having an elongate filament being extended between said terminal ends of said arms of the respective floss holder, said elongate filaments each comprising a length of dental floss;

said elongate filaments each having a pair of opposite ends; and one of said ends of each elongate filament being embedded in said terminal end of one of said arms of the respective floss holder and the other of said ends of each elongate filament being embedded in said terminal end of the other of said arms of respective floss holder;

said second flossing device having a length of about 2 inches;

a fourth packet enclosing said second flossing device therein; said fourth packet comprising a tearable and translucent material to permit viewing therethrough of said second flossing device;

a second packet enclosing therein an elongate filament wound into a coil, said elongate filament in said second packet comprising a length of dental floss, wherein said length of dental floss in said second packet is about 12 inches long; and a third flossing device, comprising:

an elongate shaft having a pair of opposite ends;

an elongate filament having a pair of opposite ends, said elongate filament comprising a length of dental floss;

wherein said length of dental floss is about 12 inches long which is appropriate for a single flossing of the user's teeth;

a first of said ends of said elongate filament being embedded in a first of said ends of said shaft to;

said elongate filament being wound about said shaft adjacent said first end of said shaft to form a coil around said shaft;

a second of said ends of said elongate filament being detachably attached to said shaft;

wherein said coil extends along the shaft about one sixth of the length of the shaft for permitting use of the second end as a toothpick in the mouth without said coil in the mouth and wetting said coil wherein a bead of wax is applied to said second end of said elongate filament and said shaft to detachably attach said second end of said elongate filament to said shaft;

said second end of said elongate filament being detachable from said shaft upon peeling or picking of said bead of wax off of said shaft to free said second end of said elongate filament;

wherein said elongate filament may be unwound form said shaft after said bead of wax is removed to provide an elongate portion of the elongate filament which may be used to floss the user's teeth therewith;

said shaft tapering to a toothpick point adjacent a second of said ends of said shaft, said point being adapted for serving as a toothpick;

said third flossing device having a length defined between said ends of said shaft of about 2 inches; and a third packet enclosing said third flossing device therein, said third packet comprising a tearable material, said third packet comprising a translucent material.

* * * * *